(12) United States Patent
Ruppel et al.

(10) Patent No.: US 9,039,980 B2
(45) Date of Patent: May 26, 2015

(54) SLURRY BUBBLE COLUMN REACTOR

(75) Inventors: Manfred Ruppel, Dietzenbach (DE); Thomas Gutermuth, Maintal (DE); Dag Schanke, Trondheim (NO); Pal Soraker, Trondheim (NO)

(73) Assignee: GTL.FI AG, Zurich (CH)

( * ) Notice: Subject to any disclaimer, the term of this patent is extended or adjusted under 35 U.S.C. 154(b) by 734 days.

(21) Appl. No.: 13/130,041

(22) PCT Filed: Nov. 10, 2009

(86) PCT No.: PCT/GB2009/002698
§ 371 (c)(1),
(2), (4) Date: Sep. 7, 2011

(87) PCT Pub. No.: WO2010/058164
PCT Pub. Date: May 27, 2010

(65) Prior Publication Data
US 2011/0313062 A1 Dec. 22, 2011

(30) Foreign Application Priority Data
Nov. 18, 2008 (GB) .................................. 0821094.0

(51) Int. Cl.
| | |
|---|---|
| B01J 8/22 | (2006.01) |
| C07C 1/04 | (2006.01) |
| C10G 2/00 | (2006.01) |
| B01J 8/18 | (2006.01) |

(52) U.S. Cl.
CPC .. *B01J 8/22* (2013.01); *B01J 8/224* (2013.01); *B01J 2208/00911* (2013.01); *B01J 8/226* (2013.01); *C07C 1/0415* (2013.01); *B01J 8/1818* (2013.01); *C10G 2/344* (2013.01)

(58) Field of Classification Search
None
See application file for complete search history.

(56) References Cited

U.S. PATENT DOCUMENTS

| | | | | |
|---|---|---|---|---|
| 4,166,840 | A | * | 9/1979 | Chapman ...................... 423/313 |
| 4,595,145 | A | | 6/1986 | Pratt et al. |
| 4,610,851 | A | | 9/1986 | Colvert et al. |
| 4,624,968 | A | | 11/1986 | Kim et al. |
| 5,166,072 | A | | 11/1992 | Krauling et al. |
| 5,384,336 | A | | 1/1995 | Koros |
| 5,527,473 | A | | 6/1996 | Ackerman |

(Continued)

FOREIGN PATENT DOCUMENTS

| | | |
|---|---|---|
| EP | 0592176 | 4/1994 |
| EP | 0609079 | 8/1994 |

(Continued)

OTHER PUBLICATIONS

Koch-Glitsch LP (Koch-Otto York separations technology): Mist Elimination. Jan. 1, 2007. XP002627243, pp. 3,4,9,10, retried Mar. 8, 2011. www.koch-glitsch.com/Document%20Library/ME_ProductCatalog.pdf.

(Continued)

*Primary Examiner* — Jennifer A Leung
(74) *Attorney, Agent, or Firm* — Patterson Thuente Pedersen, P.A.

(57) ABSTRACT

A slurry bubble column reactor with a gas distribution arrangement comprising an upper sparger, a lower sparger, and an open-ended tube. Gas from the lower sparger enters the tube and lowers the density of slurry in the tube. The difference in slurry density causes the slurry in the tube to rise, causing slurry outside the tube to move down, maintaining circulation and flushing catalyst from the vessel wall.

36 Claims, 3 Drawing Sheets

(56) References Cited

U.S. PATENT DOCUMENTS

| | | |
|---|---|---|
| 5,827,903 A | 10/1998 | White et al. |
| 6,160,026 A | 12/2000 | Dai et al. |
| 6,278,034 B1 * | 8/2001 | Espinoza et al. ............ 585/275 |
| 6,835,756 B2 | 12/2004 | Font Freide et al. |
| 2003/0021738 A1 | 1/2003 | Brunard et al. |
| 2003/0050348 A1 | 3/2003 | Kennedy |
| 2003/0195264 A1 | 10/2003 | Newton et al. |
| 2004/0147621 A1 | 7/2004 | Font-Freide et al. |
| 2005/0000861 A1 | 1/2005 | Clerici et al. |
| 2005/0047992 A1 | 3/2005 | Dietrich et al. |
| 2005/0113465 A1 | 5/2005 | O'Rear et al. |
| 2006/0135631 A1 | 6/2006 | Kopponen et al. |
| 2007/0197667 A1 | 8/2007 | Vogel |
| 2009/0071337 A1 | 3/2009 | Nieuwoudt |
| 2010/0137458 A1 | 6/2010 | Erling |
| 2011/0313063 A1 | 12/2011 | Soraker et al. |
| 2012/0157555 A1 | 6/2012 | Myrstad et al. |

FOREIGN PATENT DOCUMENTS

| | | | |
|---|---|---|---|
| GB | 1250222 A | * | 10/1971 |
| GB | 1265770 A | * | 3/1972 |
| GB | 2 408 744 A | | 6/2005 |
| JP | 52-054078 A | * | 5/1977 |
| WO | WO 00/63141 | | 10/2000 |
| WO | WO 03/010117 A2 | | 2/2003 |
| WO | WO 2004/026994 A1 | | 4/2004 |
| WO | WO 2004026994 | | 4/2004 |
| WO | WO 2005/005038 | | 1/2005 |
| WO | WO 2005/094979 A1 | | 10/2005 |
| WO | WO 2006/097905 A1 | | 9/2006 |
| WO | WO 2007/009952 A1 | | 1/2007 |
| WO | WO 2007/041726 | | 4/2007 |
| WO | WO 2007/065904 A1 | | 6/2007 |
| WO | WO 2007/086612 A1 | | 8/2007 |
| WO | WO 2008062208 | | 5/2008 |
| WO | WO 2008/146239 | | 12/2008 |
| WO | WO 2009/043201 | | 4/2009 |
| WO | WO 2010/072992 | | 7/2010 |

OTHER PUBLICATIONS

TWIGG, Martyn V., editor, "Catalyst Handbook," 2nd ed., Wolf Publishing Ltd. (1989), p. 195.

International Search Report for International Application No. PCT/GB2007/004484 dated Mar. 25, 2009 and GB Search Report for GB0623394.4 dated Mar. 25, 2007.

International Search Report for International Application No. PCT/GB2009/002836 dated Feb. 28, 2011 and GB Search Report for GB Application No. GB0823361.1 dated Feb. 26, 2009.

International Search Report for International Application No. PCT/GB/2010/001223 dated Mar. 21, 2011.

Application and File History for U.S. Appl. No. 12/515,933 filed Feb. 1, 2010, inventor Rytter.

Application and File History for U.S. Appl. No. 13/140,384 filed Sep. 6, 2011, inventors Soraker et al.

Steyberg and Dry (Fischer-Tropsch Technology) in studies in Surface Science and Catalysis v. 152 (2004) 700 pages.

International Search Report for International Application No. PCT/GB2011/000596 dated Jun. 30, 2011.

Application and File History for U.S. Appl. No. 13/641,847 filed Oct. 17, 2012.

* cited by examiner

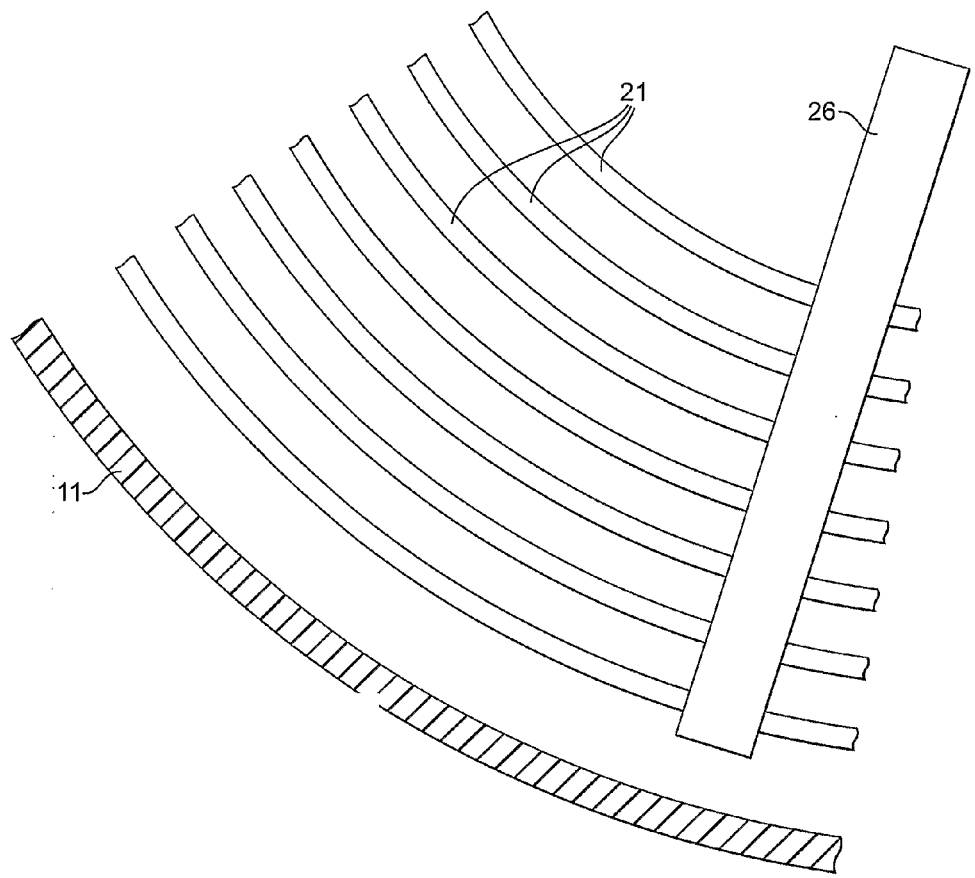
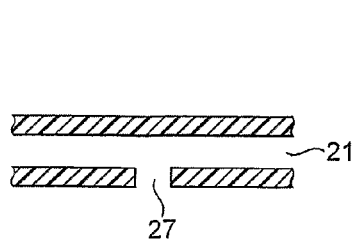 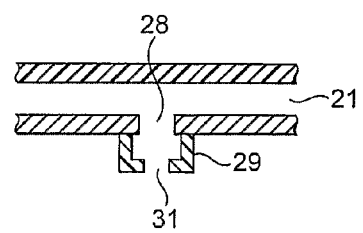
FIG. 4
FIG. 5  FIG. 6

SLURRY BUBBLE COLUMN REACTOR

RELATED APPLICATIONS

The present application is a National Phase entry of PCT Application No. PCT/GB2009/002698, filed Nov. 10, 2009, which claims priority from Great Britain Application Number 0821094.0, filed Nov. 18, 2008, the disclosures of which are hereby incorporated by reference herein in their entirety.

TECHNICAL FIELD

The present invention relates to a gas distributor arrangement in a three phase reactor or slurry bubble column reactor (SBCR).

BACKGROUND

SBCRs are employed to conduct many chemical reactions, particularly reactions in which the reactants are gaseous, the products include liquids, and a solid catalyst is required. In such a reaction, the gaseous reactants are introduced into a slurry of finely divided catalyst in a liquid medium which may contain a liquid reaction product. The gas introduction is achieved using a gas distributor.

A gas distributor for a slurry bubble column should satisfy some important requirements, which include, for example:

The gas should be rapidly mixed into the slurry, the catalyst particles should be well dispersed over a wide range of flow to the reactor, stagnant zones, especially at the bottom of the reactor, must be reduced or avoided, penetration of catalyst particles into the gas distributor must be minimized, erosion of reactor walls and internals should be reduced or avoided, the distributor should not induce unacceptable attrition of the catalyst, and the pressure drop should be low, for economic reasons.

These requirements are addressed in WO 2005/094979, for example.

SUMMARY OF THE INVENTION

It is an object of the present invention to provide a gas distributor arrangement that is simpler in design and function and simpler to operate over a wide range of flow and pressures.

According to embodiments of the invention, there is provided a slurry bubble column reactor comprising a reactor vessel having a gas outlet and a liquid outlet, and a gas distributor arrangement in the region of the bottom of the vessel when in its orientation for use, the gas distributor arrangement comprising an upper gas distributor, a lower gas distributor spaced from the upper distributor to a position nearer the bottom of the vessel, and a tube open at both ends and with its longitudinal axis extending generally vertically when the vessel is in its orientation for use, the tube being arranged so that the upper gas distributor is located close to or in the vicinity of the upper open end of the tube, and the lower gas distributor is located at a level close to the lower end of the tube, whereby in use gas from the lower sparger rings rises into the tube, reduces the density of the slurry, and causes the slurry in the tube to rise.

Thus, in use, a difference in density is established between the slurry outside the tube and the slurry inside the tube by means of the gas from the lower distributor entering the tube, and this in turn causes slurry outside the tube to flow downwards thereby sweeping the inside wall of the vessel, and then upwards through the tube as the gas from the lower distributor is entrained.

In this way, any catalyst particles with a tendency to settle at the bottom of the reactor will be kept in circulation by movement of the slurry. In addition, stagnant zones at the bottom of the reactor vessel are avoided, thereby reducing any tendency for catalyst de-activation, due to inadequate supply of reactant gases to the liquid phase.

The system reduces or avoids difficulties associated with control of the gas nozzle pressures brought about by having a series of gas manifolds with their respective nozzles at difference heights at the bottom of the reactor, which will then have to overcome different hydrostatic pressures. Independent control of the pressure to the two gas distributors means that gas can be injected through the upper gas distributor at a lower pressure than through the lower gas distributor, if desired, or even through the lower gas distributor alone.

In one embodiment, the upper gas distributor comprises a manifold arrangement with a plurality of upper nozzles. The manifold arrangement may comprise one or more pipes each having a plurality of upper nozzles. The manifold arrangement comprises a plurality of generally circular or part-circular concentric pipes each having a plurality of upper nozzles arranged along its length. The concentric pipes are tubular toroids or toroid sections.

In one embodiment, the upper nozzles all lie in a common generally horizontal plane, with height variations typically <100 mm. The diameter of the openings of the upper gas nozzles is equal to or greater than 5 mm. The openings of the upper nozzles are arranged so that the principal axis of the jets of gas produced has an inclination of 90° or less below horizontal. The upper gas distributor is connected to an upper gas supply arrangement, which gives a supply pressure to each of the nozzles with a variation between nozzle supply pressure of less than 100% of the average nozzle pressure drop.

In one embodiment, the lower gas distributor comprises a manifold arrangement with a plurality of lower nozzles. The manifold arrangement comprises one or more pipes, each having a plurality of lower nozzles. The manifold arrangement comprises a plurality of generally circular or part-circular concentric pipes each having a plurality of lower nozzles arranged along its length. The concentric pipes are tubular toroids or toroid sections.

In one embodiment, the lower nozzles all lie in a common generally horizontal plane, with variations typically <100 mm. The diameter of the openings of the lower nozzle is equal to or greater than 5 mm. The lower gas distributor is connected to a lower gas supply arrangement, which gives a supply pressure to each of the nozzles with a variation between nozzle supply pressure of less than 100% of the average nozzle pressure drop.

The upper and lower gas distributors together cover from 30 to 100% of the cross-sectional area of the reactor, and more particularly from 40 to 80%. The lower gas distributor represents from 2 to 12% of the cross-sectional area of the reactor, and more particularly from 5 to 8%. In normal operational use, the lower gas distributor is arranged to supply 4 to 20% of the gas flow to the reactor, and more particularly from 8 to 15%.

In one embodiment, the tube is cylindrical and arranged generally in the reactor with its longitudinal axis substantially vertical. The upper gas distributor is at a position between 1 m above the top of the tube and 50% of the tube length below the top of the tube. The lower gas distributor is between 0.3 m beneath and 0.3 m above the bottom of the tube. There is an open area between the reactor bottom and the tube lower end to allow slurry flow from the outside of the tube into the tube. The cross-sectional area of this is sufficient so that the average slurry velocity through this gap is slower than 5 m/s to avoid erosion of reactor bottom and attrition of catalyst particles. The velocity should however be >0.5 m/s to avoid settling of catalyst at bottom.

In one embodiment, the reactor vessel is generally cylindrical but at the bottom, there is a curved portion extending from the main cylindrical wall, a part-conical portion extending from the curved position, and a curved base. The bottom of the tube is at substantially the position where the part-conical portion joins the curved base.

Embodiments of the invention also include a method of conducting a chemical reaction involving gaseous reactants which comprises supplying the gaseous reactants to a reactor as described above, by way of the upper and lower gas distributors, in which method, the reactor contains a volume of slurry comprising a liquid phase and solid catalyst particles, and the catalyst particles are maintained in suspension in the slurry by rising gas bubbles from the gas distributors.

In one embodiment, the gas flowing through each individual nozzle exerts a dynamic pressure of less than 15 000 kg/m s$^2$, more particularly less than 10,000 kg/ms$^2$, for example a pressure in the range 200 to 8,000 kg/ms$^2$. The "dynamic pressure of the gas" is defined as the "pressure of a fluid resulting from its motion, equal to one half the fluid density times the fluid velocity squared" in Handbook of Chemistry and Physics, i.e. $q=0.5$ rv$^2$. These are exactly the same units as for kinetic energy, which is defined also in Handbook of Chemistry and Physics as the "kinetic energy per unit volume of a fluid parcel is thus 0.5 rv$^2$, where r is the density and v is the speed of the parcel." Based on the definition, kinetic energy will have the units (kg/m$^3$)*(m$^2$/s$^2$)=kg/ms$^2$.

The method can be applied to a Fischer-Tropsch synthesis reaction, for example, one in which the reaction temperature is in the range 150 to 300° C., the reaction temperature is in the range 200 to 260° C., and the reaction pressure is in the range 1 to 100 bar. In one embodiment, the temperature is in the range 210 to 250° C. and the pressure is preferably in the range 10 to 50 bar.

Embodiments of the invention also include methods of operating the reactors according to the invention to carry out reactions, to the products of those reactions and to further methods comprising various post-processing operations and to the products of such further methods.

BRIEF DESCRIPTION OF THE DRAWINGS

Embodiments of the invention can be carried into practice in various ways, and an embodiment will now be described by way of example, with reference to the accompanying drawings in which:

FIG. 4 is a top plan view of part of the upper gas distributor;

FIG. 5 is a section through a simple nozzle; and

FIG. 6 is a section through an alternative form of nozzle.

DETAILED DESCRIPTION OF THE DRAWINGS

Figure 1:
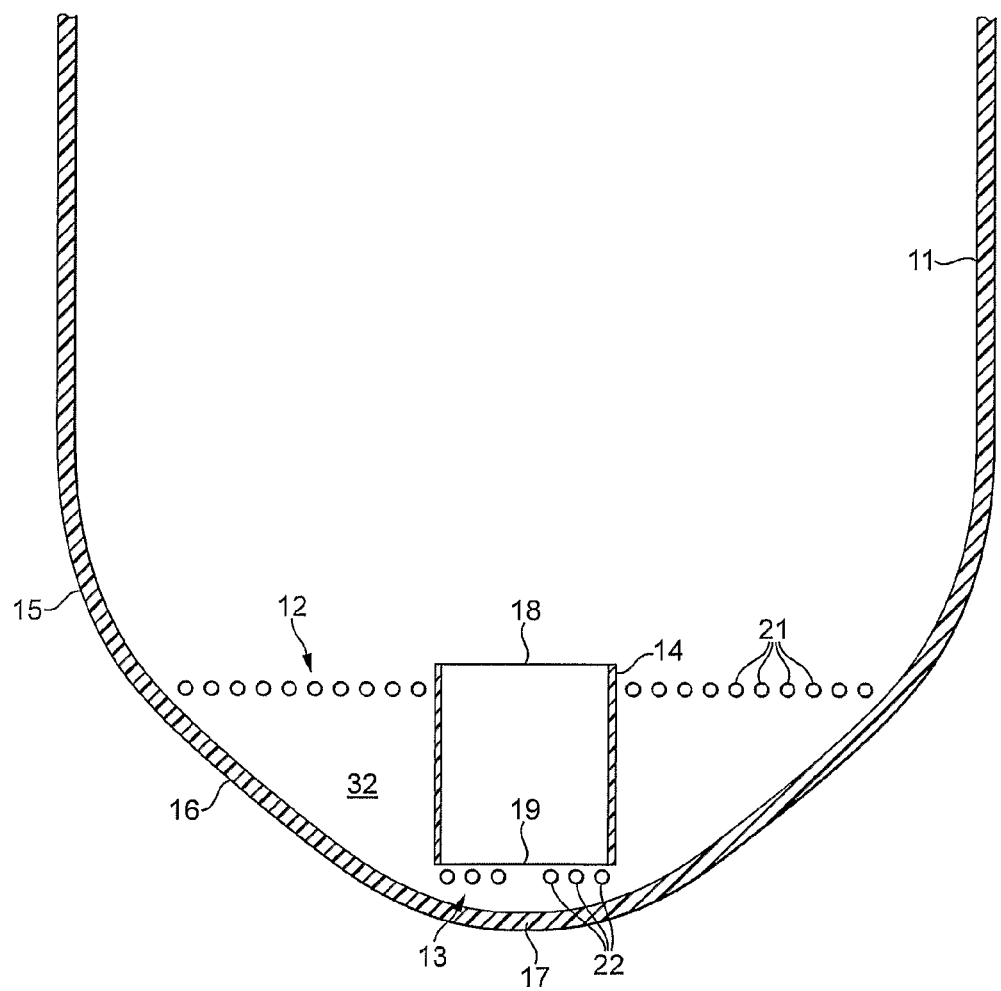
FIG. 1 is a schematic section of the bottom of a reactor vessel according to the invention.

Referring to FIG. 1, a slurry bubble column reactor comprises a vessel 11, an upper gas distributor or sparger 12, a lower gas distributor or sparger 13, and a tube 14.

The vessel 11 is generally cylindrical and has a gas outlet at the top (not shown) and a liquid product outlet (not shown). At the bottom, the vessel 11 has a curved portion 15, a part conical section 16 and a curved base 17. The tube 14 is a cylinder, open at the top 18 and bottom 19. The upper sparger 12 will be described in greater detail below with reference to FIG. 4 but includes a series of concentric tubular gas distribution rings 21 which surround the tube 14 and are located at a level just below and close to the open top 18 and just at the position where the curved portion 15 of the vessel meets the part-conical section 16. The lower sparger 13 will be described in greater detail below with reference to FIGS. 2 and 3, but includes a series of concentric tubular gas distribution rings 22 which are located within the circumference of the tube 14 and at a level close to but beneath the open bottom 19.

Figure 2:
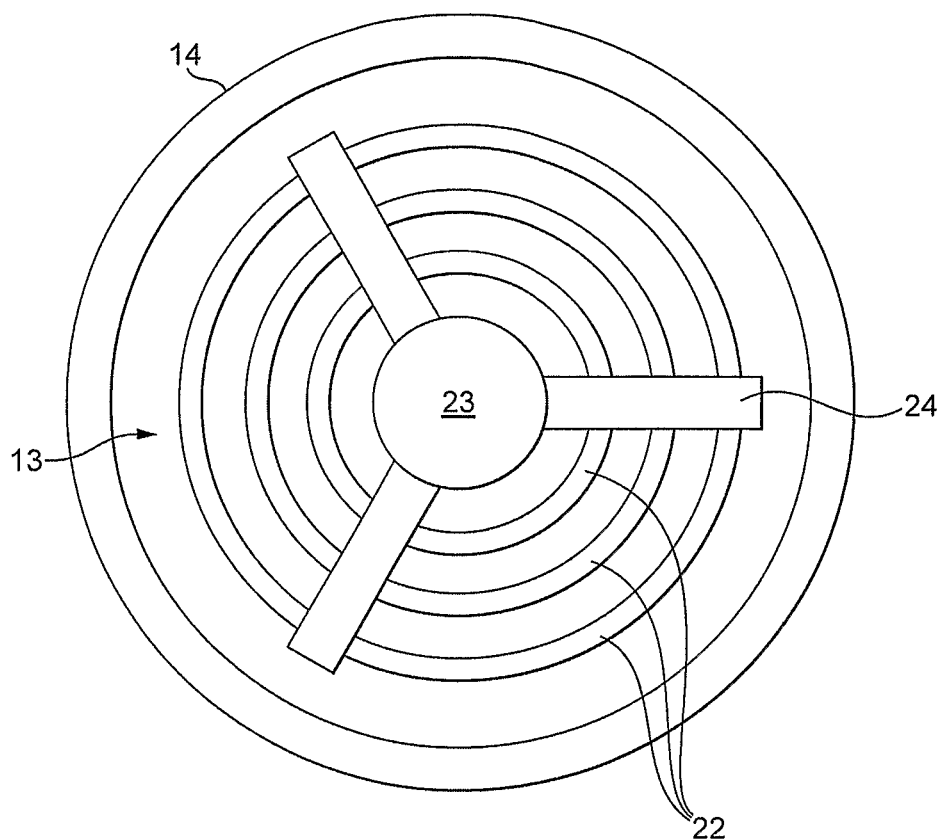
FIG. 2 is a top plan view of a lower gas distributor.
Figure 3:
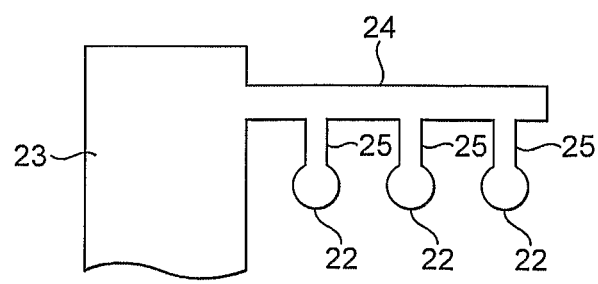
FIG. 3 is an amplified section through a part of the lower gas distributor.

Turning now to FIGS. 2 and 3, the lower sparger 13 includes a main gas feed pipe 23, three equispaced radially extending manifolds 24 connected to the feed pipe 23 and beneath the manifolds 24, the rings 22. The rings 22 are connected to the manifolds 24 by means of respective gas supply tubes 25. It will be appreciated that while three rings 22 are shown, there could be fewer or more, depending on various factors, such as the dimensions of the reactor and the rings themselves.

The upper sparger 12 is shown in FIG. 4. It consists of a main gas feed ring outside the reactor (not shown), three radically extending manifolds 26 connected to the main gas feed ring through the vessel wall 11, and beneath the manifolds 26, the rings 21. The rings 21 are connected to the manifolds 26 by means of respective gas supply tubes (not shown) in a similar fashion to the lower sparger 13. It will be appreciated that while seven rings 21 are shown in FIG. 4, there could be fewer or more, depending on various factors, such as the dimensions of the reactor and the rings 21 themselves. It will also be appreciated that a gas feed ring arrangement similar to that used for the upper sparger 12 could be used for the lower sparger 13, in place of the main gas feed pipe 23.

Each of the rings 21, 22 is formed with a series of nozzles which are generally equispaced along the ring 21, 22, and are also similarly spaced from the nozzles on adjacent rings. The nozzles are shown in more detail in FIGS. 5 and 6.

FIG. 5 shows a nozzle in the form of a simple hole 27 in a ring 21. FIG. 6 shows an alternative nozzle in the form of a hole 28 in a ring 21 covered by a cowl 29 which has an aperture 31. In each case, the hole 27 or the aperture 31 faces downwards, 90° or less below the horizontal. The L/D-ratio for the nozzle should be >1, where L is the length of the nozzle and D is the diameter of the nozzle. Where the nozzle is a simple hole as in FIG. 5, the length L is the depth of the hole, i.e. the thickness of the ring wall.

In use, the reactant gas is conveyed to the upper and lower feed pipes and enters the upper manifolds 26 and the lower manifolds 24. It then enters the respective rings 21, 22 via the respective tubes, and is injected into the slurry in the reactor vessel 11 through the nozzles. In this way, each nozzle produces a downward gas jet into the slurry. The jets near the vessel bottom create motion of the slurry near the surface of the reactor vessel 11 to prevent the catalyst from settling and keep the catalyst in motion in that area.

The flushing effect of the rings 21 of the upper sparger 12 which are further away from the vessel wall will tend to diminish. However this is addressed by the lower sparger 13. Gas from the nozzles in the lower sparger rings 22 rises into the tube 14. The density of the slurry in the tube 14 is therefore reduced. This tends to cause the slurry in the tube 14 to rise, which in turn draws slurry from the zone 32 down and into the tube 14. As this slurry descends, it flushes the wall of the vessel 11. This effect is assisted by the fact that in the region of the zone 32 the wall of the vessel 11 is the part-conical section 16.

There are several benefits to this design. Firstly, the two spargers can be designed without the need for a very narrow window for the distance between the reactor wall and the nozzles. There will be an improved turn down ratio of gas while still keeping the catalyst distributed in the liquid by using separate flow control to the two levels of sparger, the gas distribution can be controlled over a large feed flow range. Even with feeding gas only in the inner part of the reactor, a sufficient slurry circulation can be maintained to avoid sedimentation of catalyst outside the tube. The pressure drop can be kept low over the spargers due to operation at low gas velocity in sparger nozzles, but still maintain even distribution of gas, thus reducing attrition of the catalyst.

Table 1 below shows some examples for a reactor of 10 m ID. The slurry residence time below the top sparger outside tube should be as short as possible.

| Reactor shell diameter | (m) | 10 | 10 | 10 | 10 | 10 | 10 | 10 | 10 | 10 | 10 | 10 | 10 | 10 | 10 |
|---|---|---|---|---|---|---|---|---|---|---|---|---|---|---|---|
| Total Number of rings | | 11 | 11 | 11 | 11 | 11 | 11 | 11 | 11 | 11 | 11 | 11 | 11 | 11 | 11 |
| Diameter at upper sparger | (m) | 7 | 7 | 7 | 7 | 7 | 7 | 7 | 7 | 7 | 7 | 7 | 7 | 7 | 7 |
| No. of rings in lower sparger | | 4 | 4 | 4 | 4 | 3 | 3 | 3 | 3 | 2 | 2 | 2 | 2 | 4 | 4 |
| Tube diameter | (m) | 2.7 | 2.7 | 2.7 | 2.7 | 2.1 | 2.1 | 2.1 | 2.1 | 1.5 | 1.5 | 1.5 | 1.5 | 2.7 | 2.7 |
| Tube height | (m) | 1.8 | 1.8 | 1.8 | 1.8 | 1.8 | 1.8 | 1.8 | 1.8 | 1.8 | 1.8 | 1.8 | 1.8 | 1.9 | 1.9 |
| Gap between tube and reactor bottom | (m) | 0.1 | 0.2 | 0.3 | 0.4 | 0.1 | 0.2 | 0.3 | 0.4 | 0.1 | 0.2 | 0.3 | 0.4 | 0.3 | 0.3 |
| Level diff. between lower and upper sparger | (m) | 1.8 | 1.8 | 1.8 | 1.8 | 1.8 | 1.8 | 1.8 | 1.8 | 1.8 | 1.8 | 1.8 | 1.8 | 1.9 | 1.9 |
| Total coverage from sparger (% of reactor cross-sectional area) | (%) | 49 | 49 | 49 | 49 | 49 | 49 | 49 | 49 | 49 | 49 | 49 | 49 | 49 | 49 |
| Lower sparger coverage (% of reactor cross-sectional area) | (%) | 7.3 | 7.3 | 7.3 | 7.3 | 4.4 | 4.4 | 4.4 | 4.4 | 2.3 | 2.3 | 2.3 | 2.3 | 7.3 | 7.3 |
| Gas feed fraction in lower sparger (% of total gas feed) | (%) | 15 | 15 | 15 | 15 | 9 | 9 | 9 | 9 | 4.5 | 4.5 | 4.5 | 4.5 | 100 | 100 |
| Liquid superficial velocity in tube | (m/s) | 0.5 | 0.8 | 1.1 | 1.2 | 0.6 | 1.0 | 1.2 | 1.3 | 0.8 | 1.2 | 1.3 | 1.4 | 0.7 | 0.5 |
| Liquid Velocity in tube entrance | (m/s) | 3.4 | 2.8 | 2.4 | 2.0 | 3.2 | 2.6 | 2.1 | 1.7 | 3.0 | 2.2 | 1.7 | 1.3 | 1.5 | 1.1 |

Table 1 shows calculated cases for some variations of tube diameter, gap area, fraction of feed gas to the bottom sparger and bottom and top sparger coverage. The calculations are based on Bernoulli's equations for calculating the driving force for the circulation.

The invention claimed is:

1. A slurry bubble column reactor comprising:
a reactor vessel having a gas outlet and a liquid outlet, wherein a bottom of the vessel comprises a downwardly tapering part-conical portion that joins a curved base, and
a gas distributor arrangement in the region of the bottom of the vessel when in an orientation for use, the gas distributor arrangement including—
an upper gas sparger,
a lower gas sparger spaced from the upper gas sparger to a position nearer the bottom of the vessel, and
a tube having a upper end and a lower end, the tube being open at both ends, and a longitudinal axis of the tube extending generally vertically when the vessel is in the orientation for use,
wherein the upper gas sparger surrounds the outside of the tube at a position located at a level of or below the upper end of the tube, and the lower gas sparger is located at a level close to the lower end of the tube, whereby in use gas from the lower gas sparger rises into the tube, reduces a density of a slurry within the tube, and causes the slurry in the tube to rise; and
wherein the bottom end of the tube is at substantially the position where the part-conical portion joins the curved base.

2. The reactor of claim 1, wherein sparger the lower gas sparger is radially within the circumference of the lower open end of the tube.

3. The reactor of claim 1, wherein the upper gas sparger comprises one or more pipes, each having a plurality of upper nozzles.

4. The reactor of claim 3, wherein the one or more pipes comprises a plurality of generally circular or part-circular concentric pipes, each pipe having a plurality of upper gas nozzles arranged along a length of the pipe.

5. The reactor of claim 4, wherein the concentric pipes are tubular toroids or toroid sections.

6. The reactor of claim 3, wherein the upper nozzles all lie in a common generally horizontal plane.

7. The reactor of claim 3, wherein a diameter of openings of the upper nozzles is equal to or greater than 5 mm.

8. The reactor of claim 3, wherein openings of the upper nozzles are positioned such that a principal axis of jets of gas produced has an inclination of 90° or less below the horizontal.

9. The reactor of claim 3, wherein the upper nozzles have an L/D ratio >1, where L is a length of the nozzle and D is a diameter of the nozzle.

10. The reactor of claim 1, wherein the upper gas sparger is connected to an upper gas supply arrangement.

11. The reactor of claim 1, wherein the lower gas sparger comprises a manifold arrangement with a plurality of lower nozzles.

12. The reactor of claim 11, wherein the manifold arrangement comprises one or more pipes, each pipe having a plurality of lower nozzles.

13. The reactor of claim 12, wherein the one or more pipes comprises a plurality of generally circular or part-circular concentric pipes, each pipe having a plurality of lower nozzles arranged along a length of the pipe.

14. The reactor of claim 13, wherein the concentric pipes are tubular toroids or toroid sections.

15. The reactor of claim 11, wherein the lower nozzles all lie in a common generally horizontal plane.

16. The reactor of claim 11, wherein openings of the lower nozzles are positioned such that a principal axis of jets of gas produced has an inclination of 90° or less below the horizontal.

17. The reactor of claim 11, wherein a diameter of openings of the lower nozzle is equal to or greater than the 5 mm.

18. The reactor of claim 11, wherein the lower nozzles have an L/D ratio >1, where L is a length of the nozzle and D is a diameter of the nozzle.

19. The reactor of claim 1, wherein the lower gas sparger is connected to a lower gas supply arrangement.

20. The reactor of claim 1, wherein the upper and lower gas spargers together represent from 30 to 100% of a cross-sectional area of the reactor.

21. The reactor of claim of claim 20, wherein the upper and lower gas spargers together represent from 40 to 80% of the cross-sectional area of the reactor.

22. The reactor of claim 20, wherein the lower gas sparger represents from 2 to 12% of a cross-sectional area of the reactor.

23. The reactor of claim 22, wherein the lower gas sparger represents from 5 to 8% of the cross-sectional area of the reactor.

24. The reactor of claim 1, wherein the lower gas sparger is adapted to supply 4 to 20% of gas flow to the reactor.

25. The reactor of claim 24, wherein the lower gas sparger is adapted to supply 8 to 15% of the gas flow to the reactor.

26. The reactor of claim 1, wherein the tube is cylindrical and positioned generally in the reactor such that a longitudinal axis of the tube is substantially vertical.

27. The reactor of claim 1, wherein the upper gas sparger is located between the level of the upper end of the tube and half way up the tube.

28. The reactor of claim 27, wherein the upper gas sparger is at a position less than 10% of the height of the tube beneath the top end of the tube.

29. The reactor of claim 1 wherein the lower gas sparger is located at a level between 3 m above and 3 m beneath the lower end of the tube.

30. The reactor of claim 1, wherein beneath a main cylindrical portion of the vessel, the bottom of the vessel comprises a curved portion extending from the main cylindrical portion, the part-conical portion extending from the curved position, and the part-conical portion joining the curved base.

31. A method of conducting a chemical reaction involving gaseous reactants, the method comprising:
 providing a slurry bubble column reactor comprising—
  a reactor vessel having a gas outlet and a liquid outlet, wherein a bottom of the vessel comprises a downwardly tapering part-conical portion that joins a curved base, and
  a gas distributor arrangement in the region of the bottom of the vessel when in an orientation for use, the gas distributor arrangement including—
   an upper gas sparger,
   a lower gas sparger spaced from the upper gas sparger to a position nearer the bottom of the vessel, and
   a tube having a upper end and a lower end, the tube being open at both ends, and a longitudinal axis of the tube extending generally vertically when the vessel is in the orientation for use,
  wherein the upper gas sparger surrounds the outside of the tube at a position located at a level of or below the upper end of the tube, and the lower gas sparger is located at a level close to the lower end of the tube, whereby in use gas from the lower gas sparger rises into the tube, reduces a density of a slurry within the tube, and causes the slurry in the tube to rise, and wherein the bottom end of the tube is at substantially the position where the part-conical portion joins the curved base; and
 supplying the gaseous reactants to the reactor by way of the upper and lower gas spargers,
 wherein the reactor contains a volume of slurry comprising a liquid phase and solid catalyst particles, and the catalyst particles are maintained in suspension in the slurry by rising gas bubbles from the gas spargers.

32. The method of claim 31, wherein gas flowing through each individual nozzle of at least one of the upper gas sparger and the lower gas sparger exerts a dynamic pressure of less than 15 000 kg/m s$^2$.

33. The method of claim 31, wherein a difference in density is established between the slurry outside the tube and the slurry inside the tube by means of the gas from the lower gas sparger entering the tube, such that slurry outside the tube flows downwards thereby sweeping an inside wall of the vessel, and then upwards through the tube as the gas from the lower gas sparger is entrained.

34. The method of claim 31, wherein the reaction is a Fischer-Tropsch synthesis, wherein a reaction temperature is in a range from 150 to 300° C., and wherein a reaction pressure is in a range from 1 to 100 bar.

35. The method of claim 34, wherein the reaction temperature is in a range from 200 to 260°C., and the reaction pressure is in a range from 10 to 50 bar.

36. A slurry bubble column reactor comprising:
 a reactor vessel having a gas outlet and a liquid outlet, wherein beneath a main cylindrical portion of the vessel a bottom of the vessel comprises a curved portion extending from the main cylindrical portion, a downwardly tapering part-conical portion extending from the curved portion, and the part-conical portion joining a curved base; and
 a gas distributor arrangement in the region of the bottom of the vessel when in an orientation for use, the gas distributor arrangement including—
  an upper gas sparger,
  a lower gas sparger spaced from the upper gas sparger to a position nearer the bottom of the vessel, and
  a tube having a upper end and a lower end, the tube being open at both ends, and a longitudinal axis of the tube extending generally vertically when the vessel is in the orientation for use,
 wherein the upper gas sparger surrounds the outside of the tube at a position located at a level of or below the upper end of the tube, and the lower gas sparger is located at a level close to the lower end of the tube, whereby in use gas from the lower gas sparger rises into the tube, reduces a density of a slurry within the tube, and causes the slurry in the tube to rise; and
 wherein the bottom end of the tube is at substantially the position where the part-conical portion joins the curved base.

\* \* \* \* \*